US009895302B2

(12) United States Patent  
Pohlmann et al.

(10) Patent No.: US 9,895,302 B2
(45) Date of Patent: Feb. 20, 2018

(54) FINASTERIDE POLYMERIC NANOPARTICLE, AQUEOUS SUSPENSION CONTAINING THE SAME, COMPOSITION FOR THE TREATMENT OF ALOPECIA, PROCESS OF PREPARATION OF SAID COMPOSITION, AND ITS USE

(71) Applicants: Biolab Sanus Farmaceutica Ltda., Taboao da Serra (BR); Universidade Federal Do Rio Grande Do Sul—UFRGS, Porto Alegre (BR)

(72) Inventors: Adriana Raffin Pohlmann, Porto Alegre (BR); Denise Duarte Jornada, Porto Alegre (BR); Silva Staniscuaski Guterres, Porto Alegre (BR)

(73) Assignees: Biolab Sanus Farmaceutica Ltda., Taboao da Serra (BR); Unidersidade Federal Do Rio Grande Do Sul—UFRGS, Porto Alegre (BR)

( * ) Notice: Subject to any disclaimer, the term of this patent is extended or adjusted under 35 U.S.C. 154(b) by 267 days.

(21) Appl. No.: 14/424,662

(22) PCT Filed: Aug. 30, 2013

(86) PCT No.: PCT/BR2013/000334
§ 371 (c)(1),
(2) Date: Feb. 27, 2015

(87) PCT Pub. No.: WO2014/032151
PCT Pub. Date: Mar. 6, 2014

(65) Prior Publication Data
US 2015/0238406 A1 Aug. 27, 2015

(30) Foreign Application Priority Data

Aug. 31, 2012 (BR) .............................. 102012022034

(51) Int. Cl.
| A61K 8/63 | (2006.01) |
| A61K 31/58 | (2006.01) |
| A61K 9/00 | (2006.01) |
| A61Q 7/00 | (2006.01) |
| A61K 8/02 | (2006.01) |
| A61K 9/06 | (2006.01) |
| A61K 9/51 | (2006.01) |
| A61K 8/04 | (2006.01) |
| A61K 8/06 | (2006.01) |
| A61K 8/35 | (2006.01) |
| A61K 8/37 | (2006.01) |
| A61K 8/49 | (2006.01) |
| A61K 8/85 | (2006.01) |
| A61K 9/08 | (2006.01) |
| B82Y 5/00 | (2011.01) |

(52) U.S. Cl.
CPC .............. *A61K 8/63* (2013.01); *A61K 8/0241* (2013.01); *A61K 8/044* (2013.01); *A61K 8/06* (2013.01); *A61K 8/35* (2013.01); *A61K 8/37* (2013.01); *A61K 8/4973* (2013.01); *A61K 8/85* (2013.01); *A61K 9/0014* (2013.01); *A61K 9/06* (2013.01); *A61K 9/08* (2013.01); *A61K 9/5153* (2013.01); *A61K 31/58* (2013.01); *A61Q 7/00* (2013.01); *A61K 2800/412* (2013.01); *A61K 2800/5922* (2013.01); *A61K 2800/654* (2013.01); *B82Y 5/00* (2013.01)

(58) Field of Classification Search
None
See application file for complete search history.

(56) References Cited

U.S. PATENT DOCUMENTS

| 2006/0204588 A1 | 9/2006 | Liversidge et al. |
| 2009/0104291 A1 | 4/2009 | Kanazawa |
| 2011/0111019 A1 | 5/2011 | Pirot et al. |
| 2011/0117045 A1 | 5/2011 | Aimi et al. |
| 2011/0212167 A1 | 9/2011 | Ali et al. |

FOREIGN PATENT DOCUMENTS

| WO | 2005000258 A1 | 1/2005 |
| WO | 2010045292 A2 | 4/2010 |

OTHER PUBLICATIONS

Pohlmann et al. (WO 2010/040194 A2).*
Nam et al. (WO 2005/000258 A1).*
Guterres et al. ("Polymeric Nanoparticles, Nanospheres and Nanocapsules, for Cutaneous Applications", 2007).*
Sinha et al. (Poly-E-caprolactone microspheres and nanospheres: an overview, 2004).*
Unc et al. ("Commonly Used Emulsifiers and Their HLB Values").*
Drake et al., "The effects of finasteride on scalp skin and serum androgen levels in men with androgenetic alopecia." Journal of the American Academy of Dermatology, 1999, vol. 41, No. 4, p. 550-554.
Inui et al., "Molecular basis of androgenetic alopecia: From androgen to paracrine mediators through dermal papilla." Journal of Dermatological Science, 2011, vol. 61, p. 1-6.
Trueb, "Molecular mechanisms of androgenetic alopecia." Experimental Gerontology, 2002 v. 37, No. 8-9, p. 981-990.
Liu et al. "Different patterns of 5α-reductase expression, cellular distribution, and testosterone metabolism in human follicular dermal papilla cells." Biochemical and Biophysical Research Communications, 2008, 368 p. 858-864.

(Continued)

Primary Examiner — Robert A Wax
Assistant Examiner — Quanglong N Truong
(74) Attorney, Agent, or Firm — Reed Smith LLP; Matthew P. Frederick; Ryan P. Cox

(57) ABSTRACT

The present invention aims to provide a pharmaceutical composition for the treatment of alopecia, said composition comprising polymeric nanoparticles, preferably nanocapsules, containing finasteride, additives and a pharmaceutically acceptable carrier, as well as the use of the nanoparticles for preparing said composition for treating alopecia. The invention further includes an appropriate finasteride nanocapsule preparation process suitable for a composition for topical application for treating alopecia.

6 Claims, 6 Drawing Sheets

(56) References Cited

OTHER PUBLICATIONS

Ellis, "The genetics of androgenetic alopecia." Clinics in Dermatology, 2001, vol. 19, p. 149-154.
Sinclair, "Male androgenetic alopecia." The Journal of Men's Health & Gender, 2004 v. 1, No. 4, p. 319-327.
Kumari et al., "Biodegradable polymeric nanoparticle based drug delivery systems, Colloids and Surfaces B: Biointerfaces," vol. 75, Issue 1, Jan. 1, 2010, pp. 1-18.
Torchilin et al., "Recent Advances With Liposomes as Pharmaceutical Carriers", Nature Reviews, vol. 4, Feb. 2005, p. 145-160.
Schaffazick et al., "Characterization and physicochemical stability of nanoparticle polymeric systems for drug delivery." New Chemistry, 2003, vol. 26, No. 5, p. 726-737. (with abstract).
Fessi et al., "Nanocapsule formation by interfacial polymer deposition following solvent displacement." International Journal of Pharmaceutics, 1989, vol. 55, No. 1, p. R1-R4.
Tsujimoto et al., "Evaluation of the permeability of hair growing ingredient encapsulated PLGA nanospheres to hair follicles and their hair growing effects." Bioorganic & Medicinal Chemistry Letters, 2007, vol. 17, p. 4771-4777.
Lademann et al., "Nanoparticles—An efficient carrier for drug delivery into the hair follicles." European Journal of Pharmaceutics and Biopharmaceutics, 2007, vol. 66, No. 2, p. 159-164.
Stout et al., "Finasteride Treatment of Hair Loss in Women." The Annals of Pharmacotherapy, 2010, vol. 44, No. 6, p. 1090-1097.
Matias et al., "Animal models of androgen-dependent disorders of the pilosebaceous apparatus. 1. The androchronogenetic alopecia (AGA) mouse as a model for male-pattern baldness." Archives of Dermatological Research, v. 281, p. 247-253, 1989.
Papakostas, et al. "Nanoparticles in dermatology", Arch dermatol Res (2011) 303:533-550.
Venturini et al. "Formulation of lipid core nanocapsules" Colloids and Surfaces A: Physicochem. Eng. Aspects 375 (2011) 200-208.
Guterres et al. "Polymeric Nanoparticles, Nanospheres and Nanocapsules, for Cutaneous Applications" Drug Target Insights 2007:2 147-157.

* cited by examiner

FINASTERIDE POLYMERIC NANOPARTICLE, AQUEOUS SUSPENSION CONTAINING THE SAME, COMPOSITION FOR THE TREATMENT OF ALOPECIA, PROCESS OF PREPARATION OF SAID COMPOSITION, AND ITS USE

This application is the United States national stage of International Application No. PCT/BR2013/000334, filed Aug. 30, 2013, which was published under PCT Article 21 in Portuguese as International Publication No. WO 2014/032151, and which claims benefit of Brazil Patent Application No. BR102012022034-2 filed Aug. 31, 2012 which is herein incorporated by reference.

FIELD OF THE INVENTION

The present invention relates to a pharmaceutical composition for topical application for the treatment of alopecia, said composition comprising polymeric nanoparticles, preferably nanocapsules containing finasteride, additives and a pharmaceutically acceptable carrier, as well as the use of nanoparticles for preparing said composition for the treatment alopecia. The invention further includes a process for the preparation of finasteride nanocapsules that are appropriate for a topical application composition suitable for treating of alopecia.

FUNDAMENTS OF THE INVENTION

Hair loss, also called alopecia, can manifest itself in many forms. It can be irreversible in cases classified as scarring alopecia where there is the destruction of hair follicles; or reversible in non-scarred cases which have several causes and may originate from pharmacological treatments, diet, physiological or psychological stress, fungal infections, chemotherapy or genetic inheritance. Because of this, several pharmacological and non-pharmacological treatments (implants and laser applications) are being used in an attempt to reverse this situation.

In capillary therapy, in order for a drug to have the desired action, it is necessary for it to reach the hair follicle (in the epidermis), where the enzyme responsible for triggering the disease is located, without permeating the blood capillaries that supply the hair follicle (avoiding a systemic action). Thus, for a formulation to be effective, it is necessary for it to be able to promote the penetration and retention of the drug at its site of action (DRAKE, L., et al.; "The effects of finasteride on scalp skin and serum androgen levels in men with androgenetic alopecia." Journal of the American Academy of Dermatology, 1999, vol. 41, no. 4, p. 550-554).

Androgenic alopecia is the transformation of mature hair follicles (terminal) to immature follicles (vellus) through successive capillary cycles with a shortening of the anagen time phase. Thus, due to the reduction in time of growth and development of the shaft, it becomes progressively shorter, thinner and often without color (INUI, S.; ITAMI, S.; "Molecular basis of androgenetic alopecia: From androgen to paracrine mediators through dermal papilla." Journal of Dermatological Science, 2011, vol. 61, p. 1-6). This is the most common type of alopecia and it affects mainly men, being related, among other factors, to the regulation of sex hormones. A greater understanding of androgenic alopecia came from the studies of Hamilton (1942) who described the pattern of hair loss and physiology as a process linked to a genetic predisposition of the hair follicle that occurs under the influence of androgens (Trueb, R M; "Molecular mechanisms of androgenetic alopecia. "Experimental Gerontology, 2002 v. 37, no. 8-9, p. 981-990). However, there is no correlation between androgenic alopecia and testosterone levels, free testosterone and bioavailable testosterone. It is probable that the pathogenic bases of baldness are mediated through intracellular signaling in the hair follicle (INUI, S.; ITAMI, S.; "Molecular basis of androgenetic alopecia: From androgen to paracrine mediators through dermal papilla." Journal of Dermatological Science, 2011, vol. 61, p. 1-6).

Through the action of the 5α-reductase enzyme, testosterone is converted to a more powerful hormone dihydrotestosterone (DHT). It is believed that its action is greater than that of testosterone for two main reasons: (i) DHT cannot be converted into estrogen by aromatases, maintaining only its purely androgenic activity, (ii) in vitro studies demonstrate that DHT binds with more affinity to the androgen receptor than testosterone (LIU, S.; YAMAUCHI, H.; "Different patterns of 5α-reductase expression, cellular distribution, and testosterone metabolism in human follicular dermal papilla cells." Biochemical and Biophysical Research Communications, 2008, 368 p. 858-864). The action of these androgen hormones occurs by disseminating them through the cell membrane with the purpose of binding to the intracellular androgen receptor. As a result of this binding, the hormone-receptor complex undergoes conformational changes, thus binding the complex with the promoter site in the DNA, triggering the production of messenger RNAs that will transcribe the genetic response (INUI, S.; ITAMI, S.; "Molecular basis of androgenetic alopecia: From androgen to paracrine mediators through dermal papilla."Journal of Dermatological Science, 2011, vol. 61, p. 1-6). On the binding of DHT to the androgen receptor present in the hair follicle, the response is a decrease in the anagen phase of the hair growth cycle, thus moving the hair to the early telogen phase (Ellis, J A; Harrap, S B; "The genetics of androgenetic alopecia." Clinics in Dermatology, 2001, vol. 19, p. 149-154).

Androgenic alopecia presents a pattern in hair loss, which facilitates the diagnosis and easily distinguishes it from other types. By default, initial loss of the hair shaft occurs on the frontal part or on the vertex only, and may expand to other regions. The degree of alopecia can be determined by the Norwood-Hamilton scale. This scale identifies three types of hair loss patterns: vertex pattern (where the loss of the shaft starts at the back), front pattern (where the loss of the shaft starts at the front) and the normal pattern (beginning with loss at both the front and the back), with all patterns being divided into seven stages of hair loss (Sinclair, R D; "Male androgenetic alopecia." The Journal of Men's Health & Gender, 2004 v. 1, no. 4, p. 319-327).

Currently, the treatment of alopecia can be both topical and systemic. Among the drugs approved by ANVISA (Brazil), the following can be cited: (i) as systemic, the medicine made of finasteride (1 mg) for oral use, marketed under the brand name Propecia®, which acts as a blocker of DHT hormone; and (ii) as topicals: (a) a drug with a minoxidil base, marketed under the brand name Regain®/Rogain® mousse with 2% (for women) and 5% (for men) and (b) the drug based on alphaestradiol, marketed under the brand name Avicis® in the form of a 0.025% solution.

The active ingredient (finasteride) presents several difficulties related to stability, bioavailability and formulation that result from its physicochemical and biological/physiological properties. To solve or reduce the negative characteristics of the active ingredient, alternatives were researched to "protect it against degradation" or to "increase its solubility."

The development of new drug delivery systems has been the target of improvements directed towards the enhancement of its therapeutic efficacy and safety of use, by changing pharmacokinetic and pharmacodynamic aspects. Among the colloidal drug delivery systems, there are the polymeric nanoparticles and liposomes (Avnesh Kumari, Sudesh Kumar Yadav, Subhash C. Yadav, Biodegradable polymeric nanoparticle based drug delivery systems, Colloids and Surfaces B: Biointerfaces, Volume 75, Issue 1, Jan. 1, 2010, Pages 1-18; Vladimir P. Torchilin, RECENT ADVANCES WITH LIPOSOMES AS PHARMACEUTICAL CARRIERS, NATURE REVIEWS, VOLUME 4, FEBRUARY 2005, p 145). Because of their therapeutic potential and improved stability during storage and upon contact with body fluids, polymer nanoparticles formed by biodegradable polymers have attracted an increased attention of researchers when compared to liposomes (SCHAFFAZICK, S H, et al.; "Characterization and physicochemical stability of nanoparticle polymeric systems for drug delivery." New Chemistry, 2003, Vol. 26, no. 5, p. 726-737).

Polymeric nanoparticles are colloidal drug carrier systems which have diameters between 10 and 1000 nm and are divided, according to their supramolecular architectures, into vesicles or matrices. Nanocapsules (vesicular) have an oily core surrounded by a polymer matrix, allowing the drug to be dispersed in the core and/or adsorbed in the polymeric wall. Nanospheres (matrices) do not have an oily core, only a polymeric structure, so the drug may be adsorbed or retained in the polymer matrix. Nanoparticles made of biodegradable polymers have been preferred since they are potentially more therapeutic, and have high stability in biological fluids and during storage (SCHAFFAZICK, S H, et al.; "Characterization and physicochemical stability of nanoparticle polymeric systems for drug delivery." New Chemistry, 2003, Vol. 26, no. 5, p. 726-737).

Different physicochemical processes may be employed for the preparation of these nanoparticle systems, such as: (a) interfacial deposition of preformed polymers, (b) salting-out, and (c) emulsification-diffusion. Among the major techniques for nanocapsule preparation, the interfacial deposition of preformed polymers proposed by Fessi et al in 1989 stands out. (FESSI, H.; et al; "Nanocapsule formation by interfacial polymer deposition following solvent displacement." International Journal of Pharmaceutics, 1989, vol. 55, no. 1, p. R1-R4), wherein the polymer is dissolved in the organic solvent together with the oily component, the lipophilic surfactant and the drug or active ingredient to be encapsulated. This organic/oily phase is injected under moderate agitation, over an aqueous phase, which is composed of water and a hydrophilic surfactant. This mixture spontaneously yields nanocapsules, with average diameters between 200 and 500 nm. Finally, the organic solvent and excess water are removed.

Most topical products available for the treatment of alopecia are formulated with the active ingredients dissolved in a water-alcohol solution. However, due to the low permeability of some drugs through the keratin layer, only a fraction of the applied dose reaches the site of action, penetrating the pores and hair follicles (TSUJIMOTO, H. et al.; "Evaluation of the permeability of hair growing ingredient encapsulated PLGA nanospheres to hair follicles and their hair growing effects." Bioorganic & Medicinal Chemistry Letters, 2007, vol. 17, p. 4771-4777). As a result, hair growth using these products does not exceed consumer expectations, leading to lack of adherence to the treatment. Recent studies have confirmed the hypothesis that nanoparticles can penetrate effectively in the hair follicles (Lademann, J., et al.; "Nanoparticles—An efficient carrier for drug delivery into the hair follicles." European Journal of Pharmaceutics and Biopharmaceutics, 2007, vol. 66, no. 2, p. 159-164) reaching deep functional structures wherein they remain stored for a few days. In the case of non-particulate substances, such long term effects have not been observed in hair follicles or in the stratum corneum. In principle, the stratum corneum lacks the reservoir characteristic for topically applied substances since these substances remain localized on the surface of the skin or in the upper cell layers (which are continuously removed by peeling). Therefore, hair follicles become, in long term, the only reservoirs for non-particulate substances of topical use. These observations show that hair follicles are important targets for drug delivery, since they are surrounded by a dense network of blood capillaries and dendritic cells (Langerhans cells).

For example, the effect of nanospheres of poly (lactide-co-glycolide) (PLGA) containing three different active ingredients (Hinokitiol, glycyrrhetinic acid and 6-benzylaminopurine) for hair growth was assessed in vivo (TSUJIMOTO, H., et al.; "Evaluation of the permeability of hair growing ingredient encapsulated PLGA nanospheres to hair follicles and their hair growing effects." Bioorganic & Medicinal Chemistry Letters, 2007, vol. 17, p. 4771-4777). Analyzing the fluorescence intensity of these active ingredients in human scalp biopsies, the authors found that the nanospheres had a permeability effect in the pores 2 to 2.5 times higher when compared to the control group of the same active ingredients in a buffer solution (PBS). It was also possible to see an increase in the capillary activity, whose cycle is passed from the rest phase to the growth phase, suggesting that PLGA nanospheres may be promising carriers for drugs in hair follicles.

To date, there are few papers in the literature that report the placement of finasteride in nanoparticle systems. Document US20060204588, owned by Elan Pharma International Limited, discloses a pharmaceutical composition containing nanoparticulate finasteride (having average size less than 2000 nm) and at least one surface stabilizer which may be adsorbed by or associated with the surface of the active ingredient. As to the method of preparation of the nanoparticulate finasteride formulation, this method consists in dispersing finasteride in a liquid dispersion medium, and mechanically reducing its particle size.

Patent application US20110117045 owned by Fujifilm Corporation, is a product based on protein nanoparticles containing an active ingredient for hair treatment; the product consists of nanoparticles produced from protein (such as casein, collagen, gelatin, albumin, among others) which also contains an active ingredient that promotes hair growth, and includes finasteride and minoxidil as one of these active ingredients.

Document WO2005000258, owned by Amorepacific Corportation, describes self-assembled polymeric nanoparticles comprising an amphiphilic polymer and a physiologically active ingredient; whereby the amphiphilic polymer comprises polycaprolactone and polyethylene glycol as a hydrophobic and hydrophilic block, and the physiologically active ingredient is comprised by said amphiphilic polymer. The physiologically active ingredient can be finasteride (as specified in claim 10; see also examples 45-47) or minoxidil (see page 8, lines 8-18). The motivation of the claimed improvements, i.e., the use of an amphiphilic polymer in the formation of nanoparticles containing an active ingredient, is to reduce the colloidal instability which causes the precipitation or flocculation that occurs when a hydrophobic polymer is used in the preparation of nanoparticles.

However, it is desirable to use a homopolymer which is technically less complex and simpler to obtain than a copolymer which is actually a structure in polymer blocks, wherein the ratio of the hydrophilic and lipophilic portions is difficult to control, thus causing problems in the subsequent formation of nanoparticles, especially nanocapsules.

Furthermore, the use of block copolymers which are prepared in a 1:1 ratio of the hydrophilic and lipophilic portions causes a lack of flexibility in the hydrophile-lipophile balance (HLB) which can limit the quality of nanotechnological formulations. The possibility of varying the concentration of stabilizer (hydrophilic emulsifier or surfactant) is an advantage in preparing nanoparticles. Lipophilic homopolymers can be formulated as nanoparticles by employing stabilizers in varying proportions in the formulation, allowing an optimization of physical stability of the nanocolloids.

SUMMARY OF THE INVENTION

The present invention aims to provide a pharmaceutical composition for the topical treatment of alopecia, said composition comprising polymeric nanoparticles, preferably nanocapsules, containing finasteride, additives and pharmaceutically acceptable carrier. The invention further includes a process for the preparation of finasteride nanocapsules suitable for a topical application composition for the treatment of alopecia.

A first embodiment of the invention relates to a topical pharmaceutical composition comprising a therapeutically effective amount of polymeric nanoparticles, preferably finasteride nanocapsules, stably dispersed in a pharmaceutically acceptable carrier; and optionally containing additives.

In a second embodiment, said polymeric nanoparticles, preferably nanocapsules, are formed by preparing the organic and aqueous phases, wherein:
   (i) The organic phase comprises: (a) a hydrophobic polymer, (b) an oil or mixture of oils, (c) at least one lipophilic surfactant of low HLB, (d) a solvent and (e) finasteride; and
   (ii) The aqueous phase comprises: (f) at least one hydrophilic surfactant, and (g) water.

In a third embodiment, the invention comprises the use of polymeric nanoparticles, preferably nanocapsules, for the preparation of a pharmaceutical composition for the treatment of alopecia.

The process for preparing the composition of the invention comprises two stages. The first stage, concerns the preparation of polymeric nanoparticles, preferably the nanocapsules of the invention, comprises the steps of: (i) preparing the organic phase by dissolving the hydrophobic polymer and finasteride, an oil or mixture of oils, at least one surfactant of low HLB in an organic solvent; (ii) preparing the aqueous phase by mixing at least one hydrophilic surfactant, preferably neutral, in water; (iii) injecting the organic phase in the aqueous phase to allow for the instantaneous formation of nanostructures by the diffusion of the organic phase in the medium, while the mixture is stirred for sufficient time for such dissemination conducive to the proper encapsulation of finasteride; (iv) removing of the organic solvent to permit the recovery of the aqueous phase containing the nanocapsules.

After preparing the nanocapsules, they are suspended in a suitable carrier, optionally containing additives such as dispersants, moisturizers, emollients, thickeners, sequestering agents, preservatives, antioxidants, fragrances and the like.

DETAILED DESCRIPTION OF THE INVENTION

Figure 1:
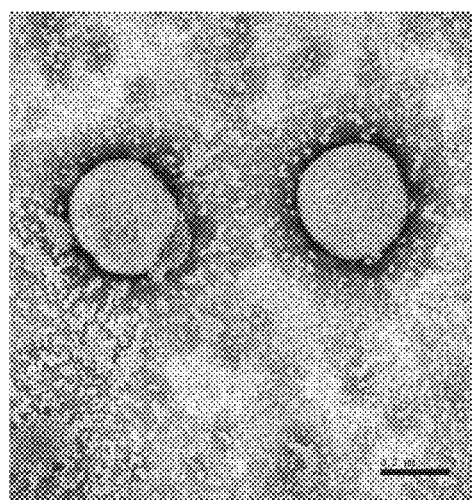
FIG. 1 shows transmission electron microscopy of the nanocapsules containing finasteride (NF25). The black bar in the right corner of the image is 0.2 micrometers.

The present invention relates to a pharmaceutical composition effective for the topical treatment of alopecia, said composition comprising nanoparticulate systems, preferably nanocapsules of finasteride, pharmaceutically acceptable carriers; and optionally containing additives.

The invention also includes a process for the preparation of polymeric nanoparticles, preferably finasteride nanocapsules, which are comprised by said composition.

Finasteride is a synthetic azosteroid with potent selective antagonist action on 5α-reductase type 2 enzymes. Finasteride acts by irreversibly binding to the enzyme, preventing the conversion of testosterone to its active metabolite, dihydrotestosterone (DHT). The use of finasteride was initially approved for the reduction of prostate size associated with urinary obstruction (benign prostatic hyperplasia), since DHT in men, although responsible for prostate growth, can be involved in development of hyperplasia. However, it has been observed that patients taking this drug also presented a reversal in alopecia symptoms. For this reason, the development of studies to investigate the potential of finasteride in the treatment of baldness had begun (Sinclair, R D, "Male androgenetic alopecia: Part II." The Journal of Men's Health & Gender, 2005, vol. 2, no. 1, p. 38-44). A study by Kaufmann et al (2008) with 1553 men aged 18 to 41 years evaluated the action of finasteride in doses of 1 mg daily against placebo for five years. The result of treatment with finasteride led to a decrease in the probability of visible hair loss, compared to the increased likelihood of visible hair loss in patients treated with placebo. In this study, at the end of the five years, 75% of placebo-treated patients developed a baldness and only 10% of patients treated with finasteride developed the disease. A review of the safety and efficacy of finasteride use for treating androgenic alopecia in women showed in conclusion that this drug can be used safely and effectively in cases wherein topical treatment with minoxidil is not effective (Stout, S M; STUMPF, J L; "Finasteride Treatment of Hair Loss in Women." The Annals of Pharmacotherapy, 2010, vol. 44, no. 6, p. 1090-1097.

The present invention avoids the disadvantages and side effects associated with systemic administration of finasteride by proposing a topical application pharmaceutical composition of finasteride for the treatment of alopecia.

The invention is based on the preparation of finasteride nanocapsules, by means of the method of interfacial deposition of preformed polymer, wherein it is firstly made the dissolution of finasteride, of a hydrophobic polymer, of at least one oil or an oil blend and at of least one surfactant of low HLB (Hydrophilic Lipophilic Balance) in an organic solvent to form the organic phase; and the mixture of at least one hydrophilic surfactant, preferably neutral, in water to form the aqueous phase.

The invention is particularly directed to the preparation of polymeric nanoparticles, preferably nanocapsules, by the method of self-organization of nanocapsules from solutions with consequent interfacial polymer deposition, due to its insolubility in both the internal and external phases of the colloidal dispersions. However, it should be clear that other methods can be used to produce the nanocapsules of the invention.

Said polymeric nanoparticles, preferably nanocapsules, are formed from the organic and aqueous phases, as follows:
(i) The organic phase comprises: (a) a hydrophobic polymer, (b) an oil or a mixture of oils, (c) at least one low HLB lipophilic surfactant, (d) a solvent and (e) finasteride; and
(ii) The aqueous phase comprises: (f) at least one hydrophilic surfactant, and (g) water.

Said polymer used to encapsulate the finasteride is a hydrophobic polymer selected from the group consisting of vinyl polymers, polyesters, polyamides, polyurethanes, acrylic polymers and polycarbonates. Preferably, the used hydrophobic polymer is a biodegradable polymer from the group of polyesters having a melting point of less than 120° C. More preferably, the biodegradable hydrophobic polymer from the group of polyesters, having a melting point of less than 120° C. is selected from the group consisting of a poly(lactide), a poly (glycolide), copolymers of poly(lactide-co-glycolide), a polycaprolactone, a copolymer of polycaprolactone with polyester, with polyamide, with polyurethane or with a vinyl polymer and most preferably, is the poly(ε-caprolactone).

The oil or oil mixture used in the preparation of the invention's organic phase of the nanocapsules is selected from the group consisting of medium chain triglyceride, canola oil, soybean oil, olive oil, rice bran oil, grape seed oil, fish oil, linseed oil, essential oils, and mixtures thereof.

Medium chain triglycerides are preferably used; wherein, among the medium-chain triglycerides are those selected from the group of caprylic and capric acids triglycerides, propylene glycol dicaprylate-caprate, oleyl macrogolglycerides, lauriola, linoleoyl and mixtures thereof. Among the essential oils are those selected from the group of linalool, farnesol and mixtures thereof.

In a first embodiment of the invention, triglycerides of caprylic and capric acids are preferably used.

And, in a second embodiment of the present invention, a triglyceride mixture of caprylic and capric acids and Unistab® S-69 is preferably used. Unistab® S-69 is a mixture of linalool and farnesol, a mixture of essential oils available on the market.

The second embodiment of the invention is to increase the encapsulation of finasteride by the addition of a new oil in the formulation's lipid core composition in which the solubility is greater than in caprylic and capric triglycerides. To this end, Unistab® S-69, a commercial mixture, was preferentially employed and consists of farnesol and linalool, in which the solubility of finasteride is about 90 mg/mL (dosing done by HPLC). Farnesol is a sesquiterpene alcohol and linalool is a terpenic alcohol, both found in various essential oils and insoluble in water but miscible with oils and other organic solvents such as acetone and ethanol. For being volatile, Unistab® S-69 was mixed with triglycerides in a ratio of 2.3: 1 (v/v) (Unistab® S-69: triglycerides). However, this proportion, considering the saturation of finasteride in Unistab® S-69, could be employed in the preparation of a formulation with a drug concentration of 2.0 mg/ml, due to the volatility of Unistab® S-69 and to the consequent loss of oil due to the draw caused by steam during the process of solvent evaporation under reduced pressure, a formulation was prepared with a finasteride concentration of 0.5 mg/ml, in order to ensure the nanometric features of the system. This formulation comprising a new lipid core represents the second embodiment of the invention.

Said lipophilic surfactant used in the organic phase of preparation of polymeric nanoparticles of the invention is a low HLB surfactant, preferably with a value in the range of 3 to 6, being solid or liquid, preferably solid, selected from the group consisting of sorbitan monostearate, sorbitan distearate, sorbitan tristearate, capryl caproyl macrogol glycerides, propylene glycol laurates, propylene glycol caprylates, glyceryl monostearate, poliglicerol oleates, or mixtures thereof. Preferably, the lipophilic surfactant used in the organic phase of the invention is sorbitan monostearate.

The solvent used in the organic phase of the preparation of these polymeric nanoparticles, preferably nanocapsules of the present invention is an organic solvent selected from the group consisting of acetone, dimethylsulfoxide, dimethylformamide, N-methylpyrrolidone, dioxane, propylene carbonate, diethyl ether, tetrahydrofuran, organohalogen, ethyl acetate, acetonitrile, methyl ethyl ketone, mixtures thereof or any other solvent that presents physicochemical properties of intermolecular interaction with water. In a preferred embodiment of the invention, the organic solvent is preferably acetone.

The aqueous phase contains at least one hydrophilic surfactant selected from the group consisting of polyoxygenated polymers, ionic surfactants and neutral surfactants. For the preparation of the polymeric nanoparticles of the invention, preferably the aqueous phase contains at least one hydrophilic surfactant preferably being an emulsifier such as polyoxygenated polymers, or ionic surfactants such as lecithin or a neutral surfactant selected from the group consisting of polysorbate 20, 60 or 80, macrogol stearate, macrogol cetostearyl ether, macrogol lauryl ether, macrogol oleyl ether, macrogol oleate, polyoxyl castor oil, hydrogenated polyoxyl castor oil, or mixtures thereof. Preferably, polysorbate is employed, and more preferably, polysorbate 80 is chosen for the aqueous phase of the nanoparticles preparation of the invention.

The following are specific embodiments of the invention. However, it should be understood that such examples are provided for illustrative purposes only, and that various modifications or changes, in light of the embodiments disclosed herein, will be suggestive to specialists in the art and must be included within the spirit and scope of this disclosure and the scope of the accompanying claims.

The aqueous suspension of polymeric nanoparticles, preferably nanocapsules comprises:
  (i) In the organic phase (a) from 0.001% to 30.0% (w/w) of a hydrophobic polymer, (b) from 0.01% to 50.0% (w/w) of an oil or mixture of oils, (c) from 0.01% to 50.0% (w/w) of at least one low HLB lipophilic surfactant, preferably solid, (d) from 10% to 80% (w/w) of an organic solvent; and (e) from 0.001% to 80% (w/w) of finasteride; and
  (ii) In the aqueous phase (f) from 0.05% to 20.0% (w/w) of at least one hydrophilic surfactant, and g from 10% to 90% (w/w) water.

In a first preferred formulation of the aqueous suspension, the polymeric nanoparticles, preferably nanocapsules, comprise:
  (i) In the organic phase (a) from 0.05% to 20.0% (w/w) of a hydrophobic polymer, preferably poly($\epsilon$-caprolactone); (b) from 0.05% to 20.0% (w/w) of an oil preferably medium-chain triglycerides; (c) from 0.05% to 20.0% (w/w) of at least one lipophilic surfactant, preferably sorbitan monostearate; (d) from 10% to 80% (w/w) of an organic solvent, preferably acetone; and (e) from 0.005% to 50% (w/w of finasteride; and In a second preferred formulation of the aqueous suspension, the polymer nanoparticles, preferably nanocapsules comprise:
  (i) In the organic phase (a) from 0.05% to 20.0% (w/w) of a hydrophobic polymer, preferably poly($\epsilon$-caprolactone); (b) from 0.05% to 20.0% (w/w) of a mixture of oils, preferably a mixture of triglycerides of caprylic and capric acids with farnesol, and linalool (Unistab® S-69); (c) from 0.05% to 20.0% (w/w) of at least one lipophilic surfactant, preferably sorbitan monostearate; and (d) from 10% to 80% (w/w) of an organic solvent, preferably acetone; and (e) from 0.005% to 50.0% (w/w) of finasteride; and
  (ii) In the aqueous phase (f) from 0.05% to 20.0% (w/w) of at least one hydrophilic surfactant, preferably polysorbate; and (g) from 10% to 90% (w/w) water.

A pharmaceutical composition for the treatment of alopecia contains: (A) the polymeric nanoparticles, preferably nanocapsules of the present invention, comprising: (a) from 0.01% to 2.5% (w/w) of finasteride; (b) from 0.1% to 10.0% (w/w) of a hydrophobic polymer, preferably poly($\epsilon$-caprolactone); (c) from 0.1% to 5.0% (w/w) of an oil and/or a mixture of oils, preferably medium-chain triglycerides and/or mixture of medium chain triglycerides, with linalool and farnesol Unistab® S-69; (d) from 0.1% to 5.0% (w/w) of at least one lipophilic surfactant of low HLB, preferably sorbitan monostearate; (e) from 0.001% to 10% (w/w) of a hydrophilic surfactant, preferably polysorbate 80; and (B) a pharmaceutically acceptable carrier, wherein the amount of the components of the nanocapsules are in percentage of the final formulation and said nanocapsules are dispersed in said pharmaceutically acceptable vehicle.

A preferred pharmaceutical composition for treatment of alopecia of the present invention is intended for topical administration and is in the form of a solution, gel or lotion.

The pharmaceutical composition for the treatment of alopecia optionally contains additives such as dispersants, surfactants, moisturizing agents, emollients, thickeners, sequestering agents, preservatives, antioxidants, fragrances and the like.

The following are specific embodiments of the invention. However, it should be understood that such examples are provided for illustrative purposes only, and that various modifications or changes, in light of the herein disclosed embodiments, will be suggestive to specialists in the art and must be included within the spirit and scope of this disclosure and the scope of the accompanying claims.

EXAMPLE 1

Nanocapsules of the Invention containing 0.25% Finasteride—The First Embodiment of the Invention

EXAMPLE 1.1

Preparation of Finasteride Nanocapsules According to a First Embodiment of the Invention (NF25)

The suspensions of finasteride nanocapsules were prepared from an organic phase and an aqueous phase, using the composition described in Table 1.

TABLE 1

Composition of the suspensions of poly ($\epsilon$-caprolactone) nanocapsules containing 0.25% of finasteride, prepared according to the first embodiment of the invention [NF25]

|  | Quantity |
|---|---|
| Organic Phase |  |
| Triglycerides of capric and caprylic acids | 3.30 mL |
| Sorbitan monostearate | 770 mg |
| Poly($\epsilon$-caprolactone) | 1000 mg |
| Acetone | 250 mL |
| Finasteride | 250 mg |
| Aqueous Phase |  |
| Polysorbate 80 | 770 mg |
| Distilled Water | 500 mL |

The polymer (poly ($\epsilon$-caprolactone)) was solubilized in the organic phase along with finasteride, triglycerides of capric acid and caprylic and low HLB surfactant (sorbitan monostearate) under moderate heating between 20° C. and 40° C. preferably at 40° C., employing acetone as solvent. The neutral surfactant (polysorbate 80) was dissolved in water to form the aqueous phase. After dissolution of all components of the organic phase and aqueous phases, the organic phase was injected, using a funnel, over the aqueous phase.

After the formation of the primary emulsion of nanocapsules of the invention, the emulsion was maintained under moderate agitation for 10 minutes and then concentrated to a final volume of 100 ml in a rotary evaporator under reduced pressure in a thermostatic bath in the evaporation flask between 10° C. and 80° C., preferably between 30° C.

and 45° C. to eliminate the solvent and the excess water to adjust the final concentration of finasteride. This formulation was called NF25.

EXAMPLE 1.2

Preparation of Nanoemulsion Finasteride (NEF25)

For comparison purposes, a finasteride nanoemulsion formulation was also prepared to a concentration of 0.25%. The method of preparation was identical to that of the finasteride nanocapsules (NF25) excluding, however, the (poly(-caprolactone)) polymer. Table 2 shows the composition of this formulation, which was designated NEF25.

TABLE 2

Nanoemulsion composition containing 0.25% of finasteride (NEF25)

|  | Quantity |
|---|---|
| Organic Phase | |
| Triglycerides of capric and caprylic acids | 3.30 mL |
| Sorbitan monostearate | 770 mg |
| Acetone | 250 mL |
| Finasteride | 250 mg |
| Aqueous Phase | |
| Polissorbate 80 | 770 mg |
| Distilled Water | 500 mL |

EXAMPLE 1.3

Physical and Chemical Characterization of Finasteride Nanocapsules 0.25% According to the First Embodiment of the Invention A. Determination of pH Determination of pH was performed by a potentiometer, calibrated with buffer solutions of pH 4.0 and 7.0, directly in the suspensions.

B. Determination of the Particle Diameter and Polydispersion Index by Multiple Light Scattering The nano-Zetasizer® equipment model ZEN 3600 ZS, Malvern, USA was used to determine the diameter and polydispersity of the nanoparticle suspension by dynamic light scattering. For this purpose, the samples were diluted in milliQ® water (filtered through a 0.45 micron filter, Millipore Millex-HP) 500 times at room temperature and the results were determined by the average of three repetitions.

C. Determination of Particle Size Distribution by Laser Diffractometry

To assess whether there is a concomitant micrometer population in the nanoparticle formulation, analyses were performed by laser diffraction (Mastersizer 2000, Malvern, UK) a technique capable of measuring particles in a wide range of diameters (from 0.02 to 2000 microns). Analyses were carried out by adding a sample of the dispersion accessory formulation containing about 100 ml of distilled water. The amount added was sufficient to achieve an obscuration between 0.02 and 0.10. To prevent interference, the background signal was measured before analysis.

D. Zeta Potential

The zeta potential of the nanocapsule suspensions was determined by electrophoresis methodology employing the nano-Zetasizer® equipment model ZEN 3600 ZS (Malvern, USA). The determination was carried out starting with 500× dilutions in a solution of 10 mM NaCl (filtered through a 0.45 micron filter, Millipore Millex-HP) and the results obtained were the average of three determinations.

E. Viscosity

The viscosity of the suspensions was measured using a vibrational viscometer (SV-10, A & D Company, Japan). To achieve this, the viscosity was measured directly in the suspensions for 30 seconds with data collection every 5 seconds at a temperature of 25±1.0° C.

Results:

The table below (Table 3) presents the pH values, diameter, polydispersion index, zeta potential and viscosity obtained for the finasteride nanocapsule formulation (NF25) of the first embodiment of the invention. The formulations (in triplicate batches) were macroscopically homogeneous, with a milky appearance and, when diluted, had a bluish tint (Tyndall effect), suggesting the presence of at least one nanoparticle population.

TABLE 3 pH, average diameter, polydispersion index, zeta potential and viscosity of the finasteride nanocapsule formulations (NF25).

| Parameters | NF25 |
|---|---|
| pH | 4.6 ± 0.1 |
| Average Diameter (nm) | 222 ± 3 |
| Polydispersion Index | 0.14 ± 0.03 |
| Zeta Potencial (mV) | −14.6 ± 0.6 |
| Viscosity (mPa · s) | 1.21 ± 0.07 |
| Finasteride Concentration (%) | 0.25 |

The pH of the nanocapsule suspension containing finasteride (NF25) stayed at around 4.5. In addition, this pH range is suitable for topical administration according to the literature (SZNITOWSKA et al., 2001).

The suspensions have a diameter of approximately 220 nm with a polydispersity of 0.14. To date, one of the few reports in literature of particulate systems for follicular topical application containing finasteride refers to microparticulate formulations of liposomes and lysosomes presenting particle size of 1.9 and 4.4 μm, respectively (TABBAKHIAN et al., 2006). Thus, formulations containing finasteride (NF25) developed in the present invention have a reduced diameter (in nanometric scale) and a narrow particle distribution as shown by the lower polydispersion index (<0.2).

The average zeta potential (for triplicate formulations) was approximately −14 mV. These values are derived by coating the particles with the polysorbate 80 surfactant used in the aqueous phase of the formulation, which prevents coalescence of the system through steric hindrance.

EXAMPLE 1.4

Transmission Electron Microscopy

For a better evaluation of the morphological characteristics of the suspensions of finasteride nanocapsules, an analysis by transmission electron microscopy was performed.

The analysis was performed with a transmission electron microscope (JEOL, JEM 1200 ExII, Electron Microscopy Center—UFRGS) operating at 80 kV. The diluted suspensions were deposited on the carbon support film in grids, negatively stained with uranyl acetate solution (2% w/v) and observed at a magnitude of 250,000 times (FIG. 1).

EXAMPLE 1.5

Study of the Stability of Finasteride Nanocapsules of the First Embodiment of the Invention To determine the stability of the finasteride nanocapsules (NF25), the following were evaluated:

A. Dosing of Finasteride in the Nanocapsules

The nanocapsule suspensions were treated with ultrasound in acetonitrile (for 30 minutes) causing dissolution of the formulation components. Dosage of finasteride was made using high performance liquid chromatography (HPLC).

The analyses were performed on Perkin Elmer chromatograph Series 200, using 210 nm visible UV detector, LiChrospher 100 RP-18 (5 μm, 250×4 mm) column, pre-column of the same material (5 μm) and isocratic mobile phase of acetonitrile:water (75:25), flow of 1 mL/min and injection volume of 100 μL.

B. Verification of the Presence of Crystals

When the concentration of a drug exceeds its solubility in oil, used in the nanocapsules nucleus, the simultaneous formation of nanocrystals may occur, which may have the same hydrodynamic radius of the formed nanocapsules, thereby generating a narrow size distribution, which is no different in respect to the nanocapsules. Additionally, over time, these crystals may suffer an increase in size by precipitation.

Thus, the monitoring of the formulation stability and the identification of the possible simultaneous presence of nanocrystals were performed by quantification of finasteride in suspensions using two techniques. Each batch was split into two samples: one was allowed to settle and the other was left free until analysis, time which it underwent agitation. For analysis, an aliquot sample was taken (at 0 and 30 days) of the supernatant of the resting sample and an aliquot of the free sample (after vortexing for 15 seconds) so that it was possible to differentiate the presence of precipitated crystals, by the reduction of drug content at the resting sample, and a possible drug degradation, by the aliquot of the stirred sample (measured by HPLC).

Results:

To check the stability of the nanocapsule formulation, three batches were evaluated at day 0 and after 30 days of storage (40° C. and relative humidity of 75%) regarding the diameter, polydispersity, zeta potential and determination of finasteride to characterize the behavior of these systems. The results are shown in Table 4.

TABLE 4

Stability results of the finasteride nanocapsules formulation (NF25) prepared in accordance with the first embodiment of the invention at 0 and 30 days (storage at 40° C. and relative humidity of 75%)

| Days | Diameter (nm) | Polydispersion Index | Zeta Potential (mV) | Assay (mg/mL) |
|---|---|---|---|---|
| 0 | 222 ± 3 | 0.14 ± 0.03 | −14.9 ± 3.0 | 2.3 ± 0.3 |
| 30 | 243 ± 5 | 0.16 ± 0.03 | −14.1 ± 1.3 | 2.6 ± 0.2 |

Figure 2:
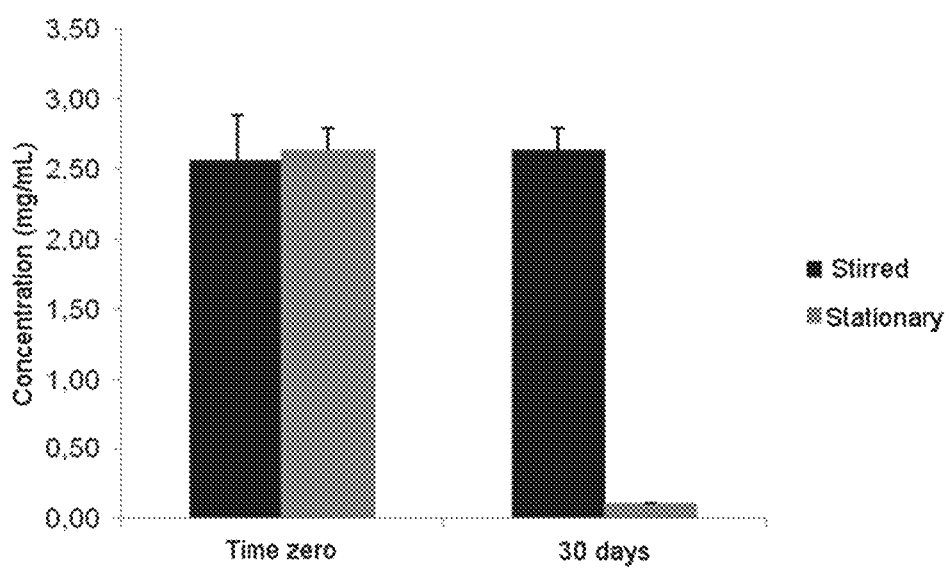
FIG. 2 shows finasteride concentrations over 30 days of the nanocapsules determined in aliquots at rest (in gray) and stirred aliquots (in black) prior to collection (both from the same lot).

During the 30 days of storage there were no significant changes in the values of diameter, polydispersion index or zeta potential. As for the dosage, the drug concentration shown on day 30 was equal to the initially used concentration. That is, the nanocapsules had a finasteride concentration similar to that used in the preparation (0.25%) with no change in size and no appearance of additional peaks in the degradation chromatogram of HPLC analysis. Noting that, in this experiment, the determinations of finasteride concentrations as a function of storage time, were performed in aliquots of suspensions subsequent to the agitation. FIG. 2 shows the results of this verification.

For the sample that was stirred prior to dosing, it can be seen that there was no decrease in the content of finasteride over the 30 days of storage, indicating that there was no degradation under these storage conditions.

EXAMPLE 1.6

In Vivo Study for Determining the Ability of Hair Recovery

For the experiments, hybrid B6CBAF1 female mice were used from the vivarium of the University of Vale do Itajai (UNIVALI). The B6CBAF1 strain of mice comes from the breeding between the female of C57BL strain and the male of CBA strain. The hybrid B6CBAF1 presents a mutation that causes the animal to develop a pathological condition of androgenic alopecia when it receives daily supplements of testosterone or dihydrotestosterone. The androgenic alopecia occurs spontaneously, being perceived through the thinning of the dorsal hair. The diffuse reduction of hair may be achieved routinely by administering 0.1 mL of a suspension with a minimum concentration of 1% of testosterone or dihydrotestosterone subcutaneously (MATIAS et al., 1989;. Sundberg et al, 1999). Thus, the animals of the strain B6CBAF1 were selected for the study employing this dosage to induce alopecia.

The animals were under standard conditions of temperature and relative humidity throughout the experiment, with light and dark cycles of 12 hours each. All animals received a subcutaneous injection of 1% testosterone dispersed in a mixture of polysorbate 80 in water (100 mg/ml) at a dose of 1 mg/day.

In the first week, the animals received only subcutaneous injections of testosterone (1). On the first day of the second week of the experiment, all animals had their hair removed from their backs with Veet® depilatory cream, for the total removal of hair. After depilation, daily injections of testosterone were maintained, and a daily topical application of the formulation was added, depending on the treatment group (placebo, treatment, control). Groups were treated with the following formulations: water (negative control), finasteride suspension in water and polysorbate 80 (positive control 1), finasteride nanoemulsion (NEF25-2 positive control) and finasteride nanocapsules (NF25).

For this test, the use of two positive controls was chosen. One composed of the drug in a coarse dispersion (in water with 0.77% polysorbate 80), with agglomerates having an average diameter (D [4.3]) of 3.2 microns and Span of 1.481 and the other composed of the nanoemulsion formulation (NEF25) with diameter of the nanometric population of 276 nm and Span 1.523 (with the presence of a small micrometer population with average diameter of 12.8 μm). The comparison with the nanoemulsion formulation was intended to verify if the nanocapsules have their effect due to their constitution (polymeric shell) or if the action takes place only by the nanoencapsulation (of part) of the drug. To monitor the growth of hair, photographs were taken on days 1, 15, and 23.

Figure 3:
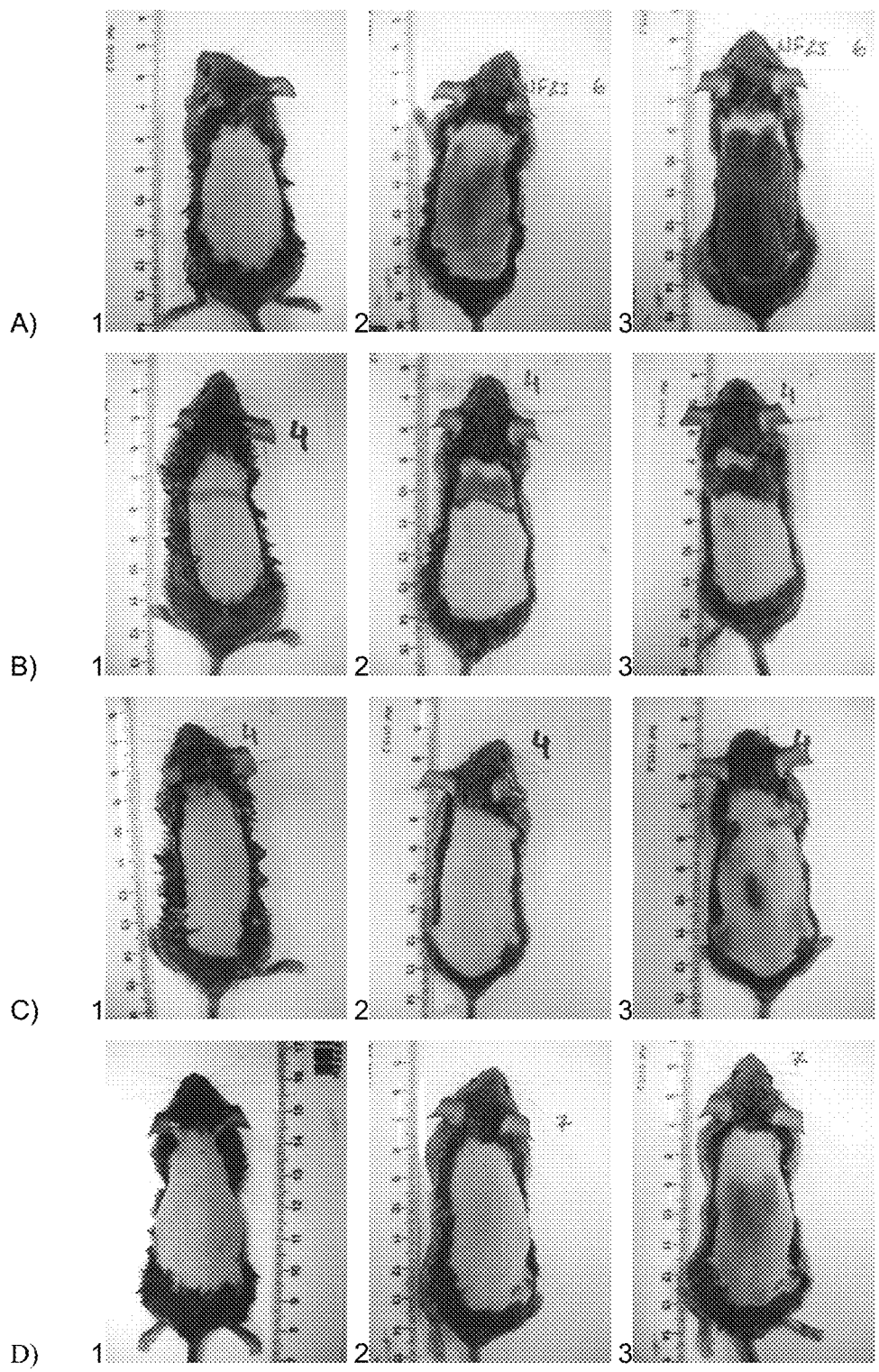
FIG. 3 shows photographs of the animals on the first day (column 1), after 15 days (column 2) and 23 days (column 3) for treatment groups treated with: NF25 (A); NEF25 (B); drug suspended in water (C) and water (D).

Results:

As can be seen in FIG. 3, treatment with finasteride nanocapsules (NF25) showed accelerated hair growth, which covered almost the entire back of the animals after 23 days. The remaining treatments recovered only small areas of the skin, and treatment with water showed only the beginning of growth. The results also demonstrated the superiority of the formulation with finasteride nanocapsules (NF25), in opposition to the nanoemulsion formulation (NEF25).

EXAMPLE 1.7

Histopathological Analysis

On the 24$^{th}$ day after the in vivo study for determining the ability of hair recovery, the animals were sacrificed by cervical dislocation to perform the histopathological examination. A small piece of skin was removed from the back of the animals (representing each group) and subjected to histological analysis in order to visualize the growth stage of the hair of each group.

To achieve this, slides were prepared and stained with hematoxylin eosin. Then, analysis was proceeded (Zeiss light microscope—First Star coupled to Canon Power Shot camera, PC1250) to determine in which growth phase the hair was found.

Figure 4:
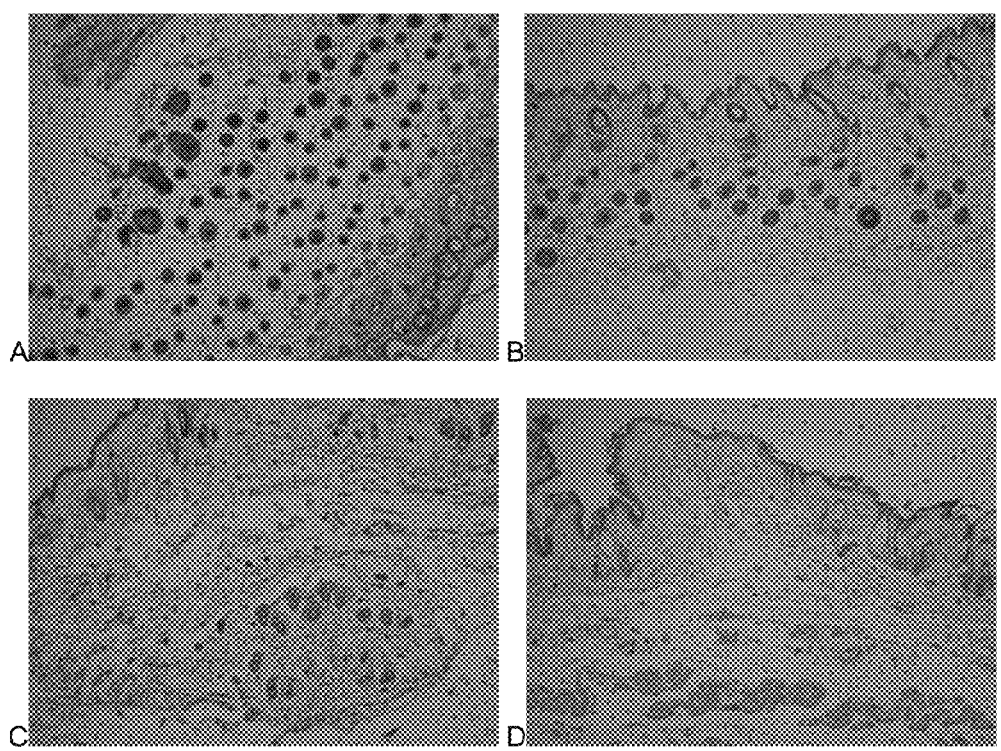
FIG. 4 shows the histological analysis of the groups: NF25 (A) NEF25 (B) C2+ (C) and C− (D).

To quantify the data obtained by histology, it was proceeded the counting of mature follicles (with pigmentation and inserted in the adipose tissue) of each of the histological slides from each group. For such, 4 slides per group were analyzed, and the counting was based on 3 different foci of the same slide, totaling 12 analyzed fields per group. For comparison between groups, statistical analysis by ANOVA ($\alpha$=0.05) was proceeded. FIG. 4 shows the results of the histopathological examination of the groups.

Histological analysis confirms the efficacy of the treatment with finasteride nanocapsules (NF25). In FIG. 4, in A (treatment with NF25), the presence of abundant terminal follicles (mature/developed) due to the strong presence of melanin (represented by the dark center of the follicle), as well as its developed based by the adipose tissue (deep insertion into the skin), which represents a terminal follicle in development can be observed. This interpretation has support in the scientific literature (Meidan et al, 2005;. VOGT et al., 2006; OTBERG et al., 2007).

In turn, for NEF25 and C2+, decreased presence of follicles with little pigmentation (or absent), located in greater amount near the dermis was observed, which characterizes an involution of terminal follicles to vellus follicles (without pigmentation and developed in the upper layers of the dermis). This interpretation has support in the scientific literature (Sinclair et al. 2003; Meidan et al, 2005;. VOGT et al., 2006; OTBERG et al., 2007).

Figure 5:
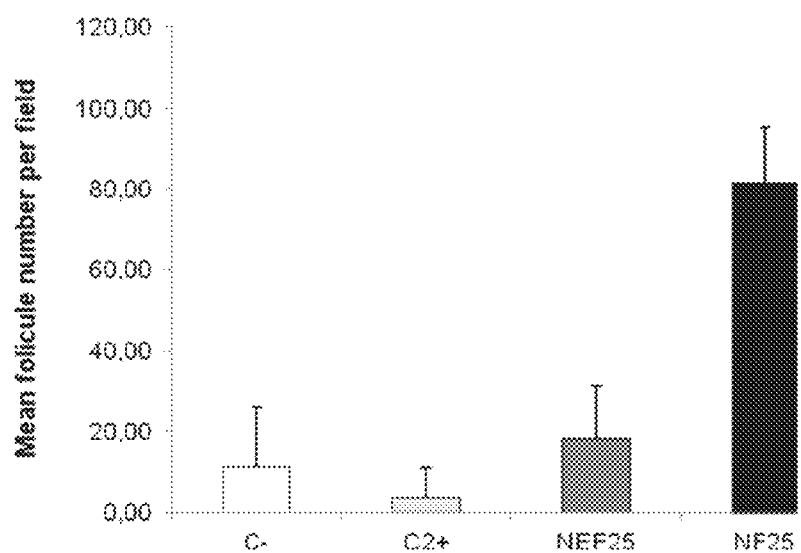
FIG. 5 shows the number of mature follicles per analyzed histologic field (n=12) for the treatments C− (water), C2+ (free drug), NEF25 (nanoemulsion) and NF25 (nanocapsules).

Additionally, based on the slides observation, the counting of mature follicles per field was analyzed. FIG. 5 shows the results based on the average number of follicles per field (n=12 fields) by evaluated group.

As can be seen in FIG. 5, there were no significant differences between water, free and finasteride nanoemulsion (NEF25) groups, which showed 11±15, 4±8 and 18±13 cells per field, respectively. In turn, the formulation of finasteride nanocapsules (NF25) showed 82±14 cells per field and was significantly higher (ANOVA, $\alpha$ 0.05) than the others. These results demonstrate that the topical formulation of finasteride nanocapsules (NF25) accelerates hair growth and development of follicles with a predisposition for androgenetic alopecia, whereas the finasteride nanoemulsion formulation (NEF25) did not show satisfactory results.

EXAMPLE 2

Nanocapsules of the Invention Containing 0.05% of Finasteride—Second Embodiment of the Invention

EXAMPLE 2.1

Preparation of Finasteride Nanocapsules According to a Second Embodiment of the Invention (NPXF05)

The suspensions of finasteride nanocapsules were prepared from an organic phase and an aqueous phase, using the composition described in Table 5.

TABLE 5

Composition of the nanocapsules suspensions of poly ($\epsilon$-caprolactone) containing 0.05% of finasteride, prepared in accordance with the second embodiment of the invention [NPXF05]

|  | Quantity |
|---|---|
| Organic Phase |  |
| Triglycerides of capric and caprylic acids | 1.00 mL |
| Unistab ® S-69 | 2.30 mL |
| Sorbitan monostearate | 770 mg |
| Poly($\epsilon$-caprolactone) | 1000 mg |
| Acetone | 250 ml |
| Finasteride | 50 mg |
| Aqueous Phase |  |
| Polisorbate 80 | 770 mg |
| Distilled Water | 500 mL |

The polymer (poly ($\epsilon$-caprolactone)) was solubilized in the organic phase along with the finasteride, the medium chain triglycerides, the Unistab® S-69 and the low HLB surfactant (sorbitan monostearate) under moderate heating between 20° C. and 40° C., preferably at 40° C., employing acetone as solvent. The neutral surfactant (polysorbate 80) was dissolved in water to form the aqueous phase. After dissolution of all components of the organic and aqueous phases, the organic phase was injected, using a funnel over the aqueous phase.

After the formation of the primary emulsion of nanocapsules of the invention, the emulsion was maintained under moderate agitation for 10 minutes and then concentrated to a final volume of 100 ml in a rotary evaporator under reduced pressure in a thermostatic bath in the evaporation flask between 10° C. and 80° C., preferably between 30° C. and 45° C. to eliminate the solvent and the excess water in order to adjust the final concentration of finasteride. This formulation was called NPXF05.

EXAMPLE 2.2

Physicochemical Characterization of Finasteride Nanocapsules 0.05% According to the Second Embodiment of the Invention (NPXF05)

A. Determination of pH

The determination of pH was performed by a potentiometer calibrated with buffer solutions of pH of 4.0 and 7.0, directly in the suspensions.

B. Determination of the Particle Diameter and Polydispersion Index by Multiple Light Scattering To determine the diameter and polydispersity of nanoparticle suspension by dynamic light scattering the nano-Zetasizer® equipment model ZEN 3600 ZS, Malvern, USA was used. For this purpose, the samples were diluted in milliQ® water (filtered through a 0.45 micron filter, Millipore Millex-HP) 500 times at room temperature and the results determined by the average of three replications.

C. Determination of Particle Size Distribution by Laser Diffractometry

To assess whether there is a concomitant micrometer population in the nanoparticle formulation, analyses were performed by laser diffraction (Mastersizer 2000, Malvern, UK) which is a technique capable of measuring particles in a wide range of diameters (from 0.02 to 2000 microns). Analyses were carried out by adding a sample of the accessory dispersion formulation containing about 100 ml of distilled water. The amount added was enough to achieve an obscuration between 0.02 and 0.10. To prevent interference, the background signal was measured before analysis.

D. Zeta Potential

The zeta potential of the nanocapsule suspensions was determined by electrophoresis methodology employing the nano-Zetasizer® equipment model ZEN 3600 ZS (Malvern, USA). The determination was carried out starting at 500 times dilution in 10 mM NaCl solution (filtered through a 0.45 micron filter, Millipore Millex-HP) and the results obtained were the average of three determinations.

E. Viscosity

The viscosity of the suspensions was measured using a vibrational viscometer (SV-10, A & D Company, Japan). For this, the viscosity was measured directly in the suspensions for 30 seconds with data collection every 5 seconds at a temperature of 25±1.0° C.

Results:

The formulation of nanocapsules prepared according to the second embodiment of the invention proved macroscopically homogeneous, with the typical odor of Unistab® S-69. The table below (Table 6) shows the pH values, diameter, polydispersion index, zeta potential and viscosity of the finasteride nanocapsules formulation (NPXF05) of the second embodiment of the invention. For comparison purposes the results of formulation NPXF05 are shown along with the ones of formulation NF25.

TABLE 6

Comparison of results of physicochemical characterization of formulations of the second and first embodiments of the invention.

| Parameters | NPXF25 (Second embodiment of the invention) | NF25 (First embodiment of the invention) |
|---|---|---|
| pH | 6.3 ± 0.1 | 4.6 ± 0.1 |
| Average Diameter (nm) | 189 ± 9 | 222 ± 3 |
| Polydispersion Index | 0.10 ± 0.05 | 0.14 ± 0.03 |
| Zeta Potencial (mV) | −9.3 ± 0.7 | −14.6 ± 0.6 |
| Viscosity (mPa · s) | 1.03 ± 0.02 | 1.21 ± 0.07 |
| Finasteride Concentration (%) | 0.05 | 0.25 |

Figure 6:
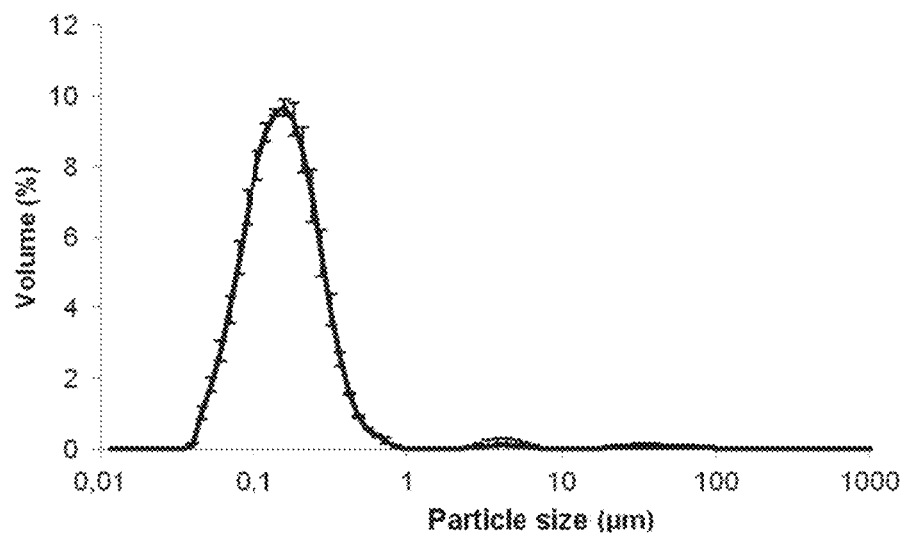
FIG. 6 shows the distribution of particle size (laser diffraction) by volume for the NPXF05 formulation.

From the physicochemical analysis it can be seen that, although modified, the formulations showed similar characteristics. However, the laser diffraction diameter analysis showed that the formulations prepared with a mixture of Unistab® S-69 and caprylic triglyceride and capric (NPXF05), containing 0.05% finasteride, showed only nano-sized populations (FIG. 6).

EXAMPLE 2.3

A Study of the Stability of Finasteride Nanocapsules of the Second Embodiment of the Invention To determine the stability of the finasteride nanocapsules (NPXF05), the following were evaluated:

A. Dosing of Finasteride in the Nanocapsules

The suspensions of nanocapsules were treated with acetonitrile in ultrasound (for 30 minutes) causing the dissolution of the formulation components. The dosage of finasteride was performed by high performance liquid chromatography (HPLC).

The analyses were performed on the Perkin Elmer chromatograph Series 200, using a 210 nm visible UV detector, LiChrospher 100 RP-18 (5 μm, 250×4 mm), a pre-column of the same material (5 microns) and an isocratic mobile phase of acetonitrile: water (75:25), flow of 1 ml/min and injection volume of 100 μL.

B. Verification of the Presence of Crystals

To verify the presence of drug dispersed in the external phase, quantification of finasteride was performed by HPLC from a freshly prepared formulation. The formulation was divided into two samples, the former was allowed to be still, and the second was stirred before the assay was carried out 30 days after their preparation. From the sample maintained still, only a supernatant aliquot was collected (preventing any movement). From the other sample, an aliquot (corresponding to 20% of the supernatant) was collected after vortexing for 15 seconds.

Figure 7:
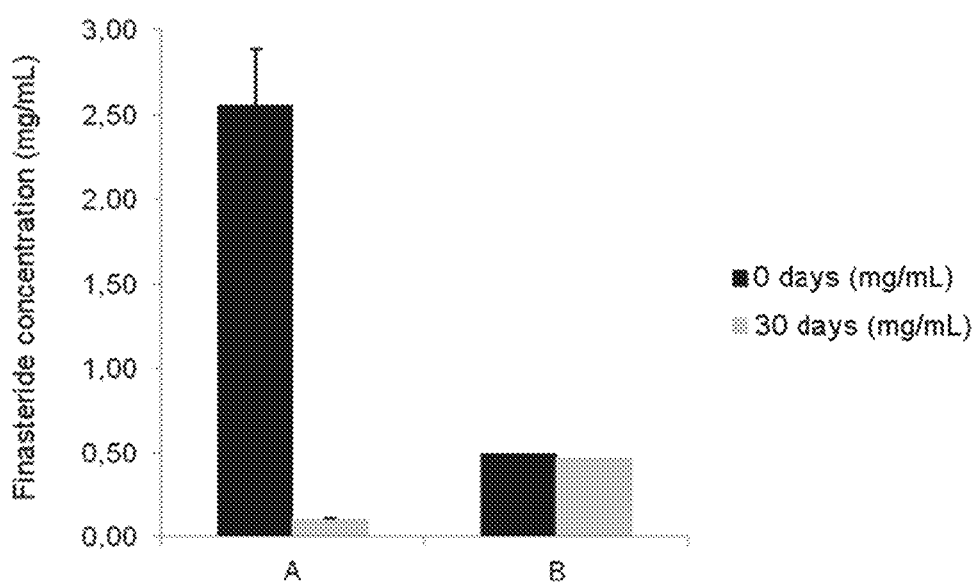
FIG. 7 shows the analysis of the percentage of drug remaining in the supernatant of the formulations (triplicate batches) NF25 (A) and NPXF05 (B), allowed to be still for 30 days.

Results:

In addition, evaluation of the sedimentation of crystals was performed (by HPLC assay of the supernatant) of triplicate NPXF25 formulations kept still for a period of 30 days. The results were compared with the ones of NF25 formulation and are shown in FIG. 7.

As noted, the addition of Unistab® S-69 to the triglycerides of caprylic and capric acids allowed a greater encapsulation of finasteride without losing the nanotechnology characteristics of the system. As noted, there was no significant decay in the active ingredient concentration on the NPXF05 formulation, which was only 4.1±0.4% compared to the original.

EXAMPLE 2.4

In Vivo Assay for Determining the Ability of Hair Recovery

For the experiments, hybrid B6CBAF1 female mice were used from the vivarium of the University of Vale do Itajai (UNIVALI). The animals were in conventional conditions of temperature and relative humidity during the experiment, with light and dark cycles of 12 hours each. All animals received a subcutaneous injection of 1% testosterone dispersed in a mixture of polysorbate 80 in water (100 mg.mL−1), at a dose of 1 mg/ day. There were five injections per week for 4 weeks.

Once more, the accelerated hair growth test was carried out, and this time the nanocapsule formulation of finasteride (NPXF05) was tested. In the first week the animals received only testosterone injections. On the first day of the second week of the experiment, all animals had their back hair removed with Veet® depilatory cream, for the total removal of hair. After removal of hair, daily injections of testosterone were maintained, and a daily topical application of the formulation was added to the treatment, depending on the treatment group (placebo, treatment, control). The test groups were the nanocapsule formulations with finasteride at 0.05% (NPXF05) prepared in accordance with the second embodiment of the invention, which were compared with the results of the finasteride nanocapsule formulation containing 0.25% (NF25) prepared according to the first embodiment of the invention.

To monitor hair growth, photographs were taken on days 0, 15, and 23.

Figure 8:
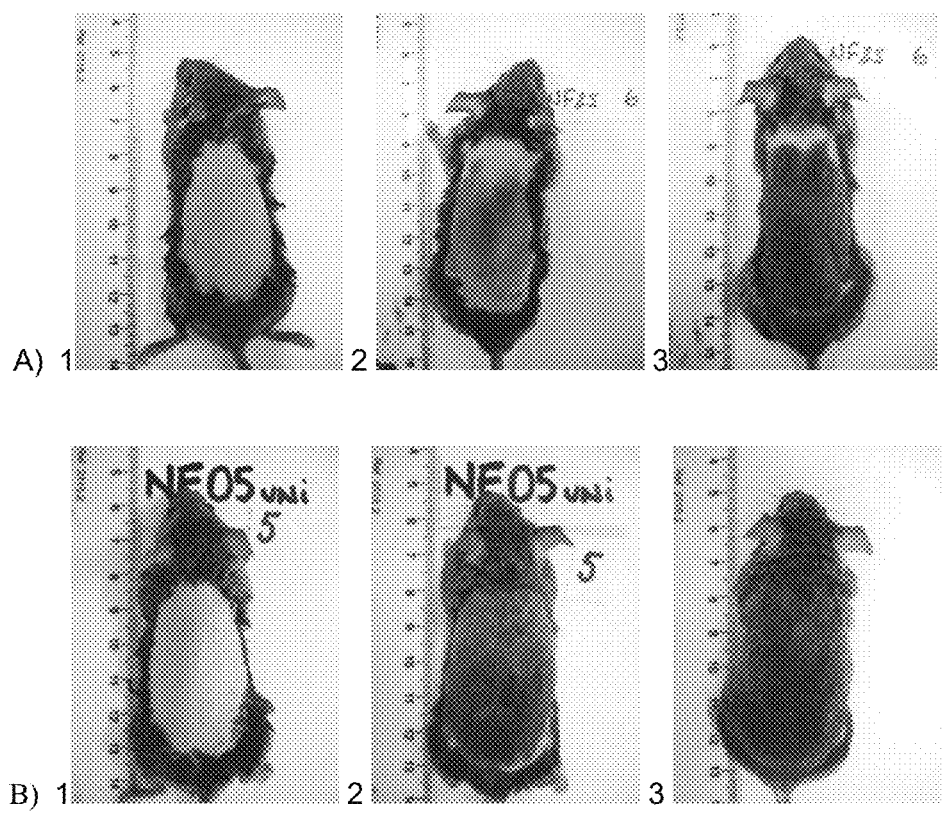
FIG. 8 shows a photograph of the animals on day 0 (photo 1) and at 15 days (photo 2) and 23 days (photo 3) of treatment groups treated with NF25 (A) and NPXF05 (B).

Results: As can be seen in FIG. 8, the nanocapsule formulation with finasteride at 0.05% (NPXF05) prepared with a combination of Unistab® S-69 and triglycerides of caprylic and capric acids showed a greater growth than the nanocapsule formulations of finasteride at 0.25% (NF25). By analyzing the photographs of the $15^{th}$ day, it is observed that the animals treated with the nanocapsule formulation of finasteride at 0.05% (NPXF05) have a bigger growth.

EXAMPLE 2.5

Histopathological Analysis

On the 24th day, after the in vivo assay for determining the ability of hair recovery, the animals were sacrificed by cervical dislocation, in order to perform the histopathological examination. A small piece of skin was removed from the backs of the animals (representing each group) and subjected to histological analysis in order to visualize the growth stage of the hair of each group.

To achieve this, slides were prepared and stained with hematoxylin eosin. Then analysis (Zeiss light microscope—First Star coupled to a Canon Power Shot camera, PC1250) was made in order to determine the growth phase in which the hair was.

To quantify data obtained by histology, counting of mature follicles (with pigmentation and inserted in the adipose tissue) of each of the histological slides of each group was made. Thus, we analyzed 4 slides per group, and the count was based on 3 different foci of the same slide, totaling 12 fields analyzed per group. For a comparison between the groups, statistical analysis by ANOVA ($\alpha=0.05$) was made.

Figure 9:
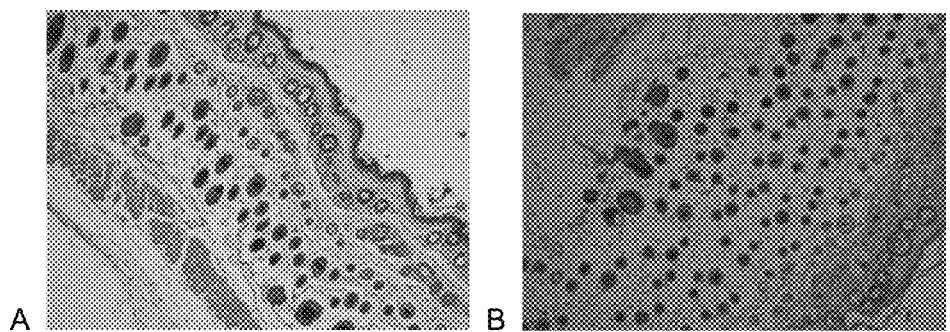
FIG. 9 shows the histopathological analysis of the skin removed from the back of the animals after 23 days of treatment with: NPXF05 (A) and NF25 (B).

FIG. 9 shows the results of histopathological examination of the groups. As can be seen in FIG. 9, the nanocapsule formulation prepared with the combination of Unistab® S-69 and triglycerides of caprylic and capric acid (NPXF05) had a higher growth than the nanocapsule formulations of finasteride (NF25). By analyzing the photographs of the $15^{th}$ day, it was observed that the animals treated with the NPXF05 formulation showed a higher growth than the others.

Figure 10:
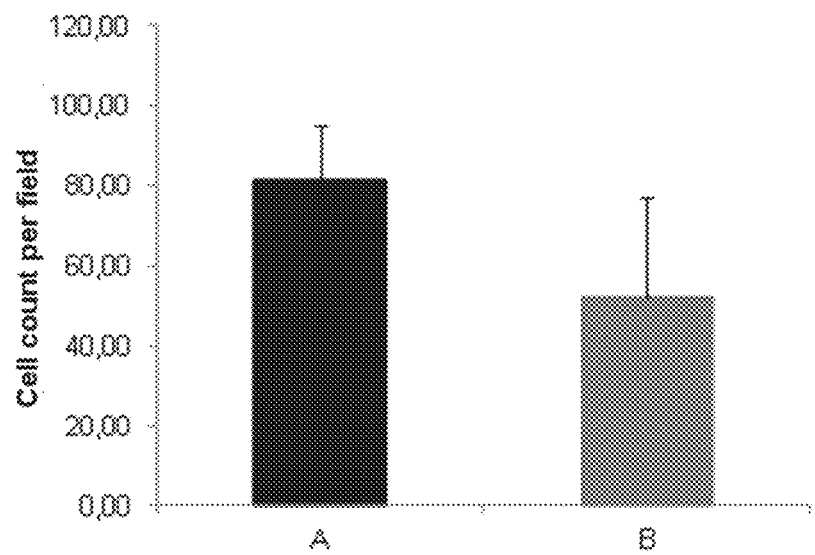
FIG. 10 shows the average number of mature follicles per field examined histologically for animals treated with the NF25 formulation (A) and the NPXF05 formulation (B).

FIG. 10 shows the average number of mature follicles per analyzed histological field. These analyses revealed that the NPXF05 formulation showed an accelerated growth and seemingly higher growth than the NF25 formulation, despite having a fewer number of mature follicles by analyzed histological field.

EXAMPLE 3

Pharmaceutical Compositions Comprising Finasteride Nanocapsules

EXAMPLE 3.A

Formulation in Form of a Topical Solution

Finasteride nanocapsules are prepared as described in examples 1.1 and 2.1. Topical solutions are prepared resulting in the formulations of Table 7.

TABLE 7

Formulations in form of a topical solution containing the suspension of nanocapsules containing 0.25% of finasteride (NF25 - first embodiment), and containing 0.05% of finasteride (NPXF05 - second embodiment)

| Components | NF25 Percentage (%, p/v) | NPXF05 Percentage (%, p/v) |
|---|---|---|
| Triglycerides of capric and caprylic acids | 3.12 | 0.95 |
| Unistab ® S-69 | — | 2.00 |
| Sorbitan Monostearate | 0.77 | 0.77 |
| Poly(ε-caprolactone) | 1.00 | 1.00 |
| Finasteride | 0.25 | 0.05 |
| Polisorbate 80 | 0.77 | 0.77 |
| Distilled Water | qsp 100 | qsp 100 |

EXAMPLE 3.B

Topical Gel Formulations

Finasteride nanocapsules are prepared as described in examples 1.1 and 2.1.

The suspension of nanocapsules prepared as described in Example 3.A, were thickened with 0.2% Carbopol® 940. Triethanolamine qs was added to obtain a suitable viscosity for topical application. The resulting gel has the formulation shown in Table 8.

TABLE 8

Formulations in the form of a topical gel containing the nanocapsule suspensions with 0.25% of finasteride (NF25 - first embodiment), and 0.05% of finasteride (NPXF05 - second embodiment)

| Components | NF25 Percentage (%) | NPXF05 Percentage (%) |
|---|---|---|
| Triglycerides of capric and caprylic acids | 3.12 | 0.95 |

TABLE 8-continued

Formulations in the form of a topical gel containing the
nanocapsule suspensions with 0.25% of finasteride
(NF25 - first embodiment), and 0.05% of finasteride
(NPXF05 - second embodiment)

| Components | NF25 Percentage (%) | NPXF05 Percentage (%) |
|---|---|---|
| Unistab ® S-69 | — | 2.00 |
| Sorbitan Monostearate | 0.77 | 0.77 |
| Poly(ε-caprolactone) | 1.00 | 1.00 |
| Finasteride | 0.25 | 0.05 |
| Polisorbate 80 | 0.77 | 0.77 |
| Carbopol 940 | 0.20 | 0.20 |
| Distilled Water | qsp 100 | qsp 100 |
| Triethanolamine | qs | qs |

EXAMPLE 3.C

Formulation in Form of a Topical Lotion

Initially, phase 1 is prepared as described in Example 3.A, using the composition from phase 1 of Table 9. Separately, the components from phase 2 were melted in a water bath at 50° C. and removed from heating after fusion. Phase 3 was added to phase 1 and dispersed under constant magnetic stirring. This mixture of phases 1 and 3 was added to the molten phase 2 and cooled to 40° C. under moderate mechanical agitation to avoid air incorporation.

TABLE 9

Formulation in form of a topical lotion containing
nanocapsule suspensions with 0.25% of finasteride
and 0.1% of finasteride.

| | NF25 Percentage (%) | NPXF053 Percentage (%) |
|---|---|---|
| Phase 1 Components | | |
| Triglycerides of capric and caprylic acids | 3.12 | 0.95 |
| Unistab ® S-69 | — | 2.00 |
| Sorbitan Monostearate | 0.77 | 0.77 |
| Poly(ε-caprolactone) | 1.00 | 1.00 |
| Finasteride | 0.25 | 0.10 |
| Polisorbate 80 | 0.77 | 0.77 |
| Distilled Water | qsp 100 | qsp 100 |
| Phase 2 Components | | |
| Coconut Oil | 2.0 | 2.0 |
| Propylparaben | 0.2 | 0.2 |
| Methylparaben | 0.1 | 0.1 |
| Phase 3 Components | | |
| Salcare SC91 (INCI: Polyacrylamide and C13-14 Isoparaffin and Laureth-7) | 2.0 | 2.0 |

All publications and patent applications mentioned in this specification are indicative of the level of those skilled in the art to which the invention relates. All publications and patent applications are incorporated herein by reference to the same extent as if each individual publication or patent application were each specifically and individually indicated to be incorporated for ease of reference.

Although certain embodiments have been described, they are presented in an exemplary mode only, and are not intended to limit the scope of the invention. In fact, the new embodiments described herein may be implemented in a variety of other forms; more than that, various omissions, substitutions and changes in the form of the embodiments described herein may be made without diverging from the spirit of the invention. The claims and their equivalents accompanying this description are considered to cover such forms or modifications as they may be within the scope and spirit of the invention.

The invention claimed is:

1. An aqueous suspension comprising polymeric nanoparticles, wherein said polymeric nanoparticles are in the form of nanocapsules containing the active ingredient finasteride formed from:
   (i) an organic phase comprising: (a) poly(ε-caprolactone), (b) a mixture of oils consisting of triglycerides of caprylic and capric acids, linalool and farnesol, (c) sorbitan monostearate, (d) acetone, and (e) finasteride; and
   (ii) an aqueous phase comprising: (f) polysorbate 80, and (g) water.

2. The aqueous suspension of polymeric nanoparticles of claim 1, wherein said aqueous suspension comprises:
   (i) in the organic phase: (a) from 0.05% to 20.0% (w/w) of poly (ε-caprolactone);
   (b) from 0.05% to 20.0% (w/w) of the mixture of oils consisting of triglycerides of caprylic capric acids, linalool and farnesol; (c) from 0.05% to 20.0% (w/w) of sorbitan monostearate; (d) from 10% to 80% (w/w) acetone; and (e) from 0.005% to 50.0% (w/w) of finasteride; and
   (ii) in the aqueous phase: (f) 0.05% to 20.0% (w/w) of polysorbate 80; and (g) from 10% to 90% (w/w) of water.

3. A pharmaceutical composition for the treatment of alopecia comprising:
   (A) the polymeric nanoparticles of claim 1 comprising 0.01 to 1.0% (w/w) of finasteride; and
   (B) a pharmaceutically acceptable carrier.

4. The pharmaceutical composition of claim 3, wherein the pharmaceutical composition is for topical administration and wherein the pharmaceutical composition is in the form of a solution, gel or lotion.

5. The pharmaceutical composition of claim 3, wherein the pharmaceutical composition further comprises at least one additive selected from the group consisting of dispersants, surfactants, moisturizing agents, emollients, thickeners, sequestering agents, preservatives, antioxidants, fragrances and mixtures thereof.

6. An aqueous suspension comprising polymeric nanoparticles, wherein said polymeric nanoparticles are in the form of nanocapsules containing the active ingredient finasteride formed from:
   (i) an organic phase comprising: (a) poly(ε-caprolactone), (b) a mixture of oils consisting of triglycerides of caprylic and capric acids, linalool and farnesol, (c) sorbitan monostearate, (d) acetone, and (e) finasteride; and
   (ii) an aqueous phase comprising: (f) polysorbate 80 and (g) water,
   wherein said nanocapsules comprise an oily core and a polymer wall, wherein the oily core comprises the mixture of oils consisting of triglycerides of caprylic and capric acids, linalool and farnesol and finasteride, and wherein the polymer wall comprises poly(ε-caprolactone).

* * * * *

UNITED STATES PATENT AND TRADEMARK OFFICE
CERTIFICATE OF CORRECTION

PATENT NO. : 9,895,302 B2
APPLICATION NO. : 14/424662
DATED : February 20, 2018
INVENTOR(S) : Pohlmann et al.

Page 1 of 1

It is certified that error appears in the above-identified patent and that said Letters Patent is hereby corrected as shown below:

On the Title Page

Item (72)

Inventor name is shown as:
"Denise Duarte Jornada"
The inventor name should read:
-- Denise Soledade Jornada --

Inventor name is shown as:
"Silva Staniscuaski Guterres"
The inventor name should read:
-- Silvia Stanisçuaski Guterres --

Signed and Sealed this
Eighteenth Day of June, 2019

Andrei Iancu
*Director of the United States Patent and Trademark Office*